United States Patent [19]

Ichikawa

[11] Patent Number: 4,783,654
[45] Date of Patent: Nov. 8, 1988

[54] RADIO PAGING SYSTEM CAPABLE OF TRANSMITTING COMMON INFORMATION AND RECEIVER THEREFOR

[75] Inventor: Yoshio Ichikawa, Tokyo, Japan

[73] Assignee: NEC Corporation, Tokyo, Japan

[21] Appl. No.: 818,642

[22] Filed: Jan. 14, 1986

[30] Foreign Application Priority Data

Jan. 14, 1985 [JP] Japan ............................. 60-4726

[51] Int. Cl.$^4$ ............................................. H04Q 7/00
[52] U.S. Cl. ............................. 340/825.44; 340/311.1; 455/38
[58] Field of Search ...................... 340/825.44, 825.03, 340/825.04, 825.36, 825.47, 825.48, 825.57, 825.62, 825.69, 311.1; 455/38, 31, 343; 379/57, 56

[56] References Cited

U.S. PATENT DOCUMENTS

| | | | |
|---|---|---|---|
| 4,353,065 | 10/1982 | Mori | 340/825.44 |
| 4,369,443 | 1/1983 | Giallanza et al. | 340/825.47 |
| 4,383,257 | 5/1983 | Giallanza et al. | 340/825.44 |
| 4,398,192 | 8/1983 | Moore et al. | 340/825.44 |
| 4,403,212 | 9/1983 | Masaki | 340/825.44 |
| 4,523,332 | 6/1985 | Mori | 340/825.44 |

FOREIGN PATENT DOCUMENTS

| | | | |
|---|---|---|---|
| 95750 | 12/1983 | European Pat. Off. | |
| 0189089 | 6/1986 | European Pat. Off. | 340/825.44 |
| 0051801 | 4/1971 | Japan | 455/343 |
| 0041044 | 3/1982 | Japan | 379/57 |
| 0041045 | 3/1982 | Japan | 379/56 |
| 2110850 | 6/1983 | United Kingdom | 379/57 |
| 2110851 | 6/1983 | United Kingdom | 379/57 |
| 2117543 | 10/1983 | United Kingdom | |

OTHER PUBLICATIONS

"Digital Display Radio Paging System", Nagata, et al., NEC R÷D, No. 68, Jan. 1983.

Primary Examiner—John W. Caldwell, Sr.
Assistant Examiner—Edwin C. Holloway, III
Attorney, Agent, or Firm—Sughrue, Mion, Zinn, Macpeak & Seas

[57] ABSTRACT

A radio paging system for transmitting address signals and messages, as well as information common to a plurality of receivers, and a receiver applicable to such a system. The radio paging system includes: an encoder which produces a first code, followed by a string of address codes each of which is followed by message codes, and a second code followed by a string of information codes, a transmitter for transmitting a string of codes produced by the encoder; and a receiver which upon detection of the first code produces an alert signal and displays the message codes when the address code agrees with an address code stored in memory, and which, upon detection of the second code, displays the information codes which follow.

11 Claims, 9 Drawing Sheets

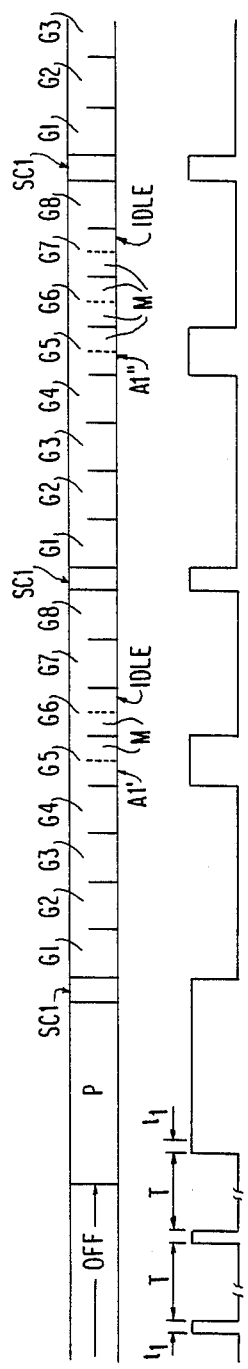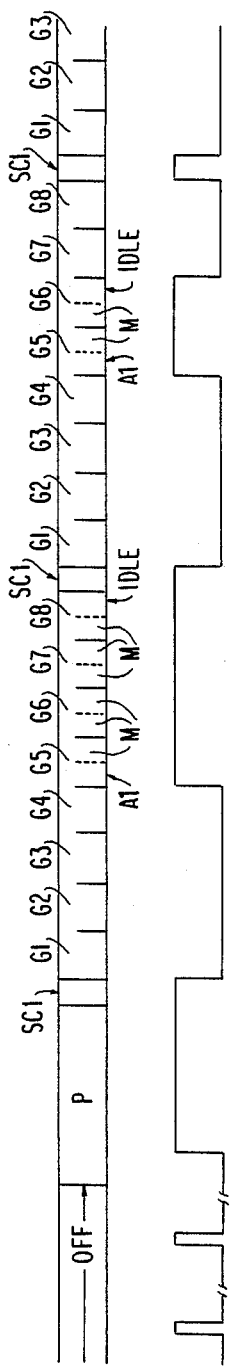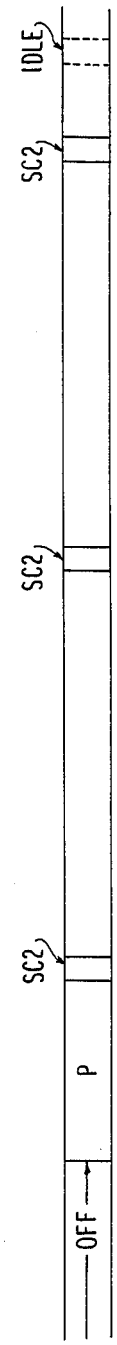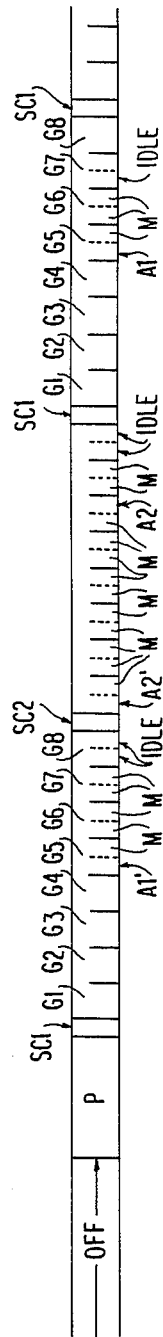
FIG.10a  FIG.10b  FIG.10c  FIG.10d  FIG.11a  FIG.11b  FIG.14a  FIG.14b

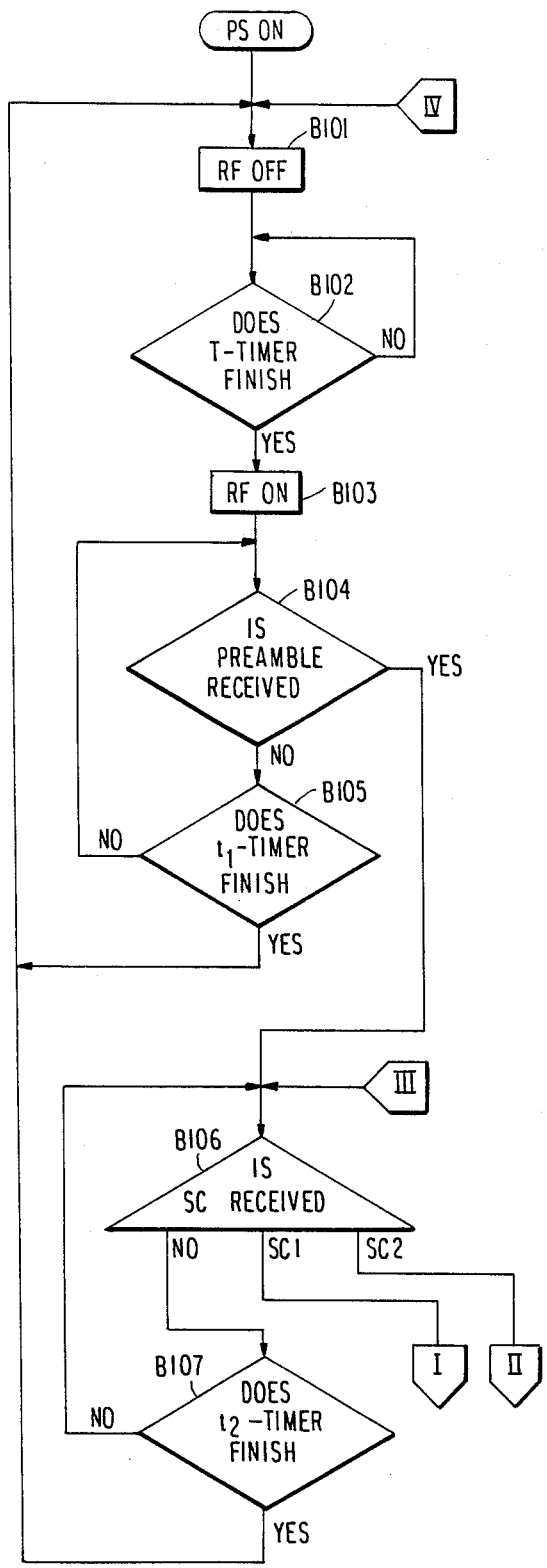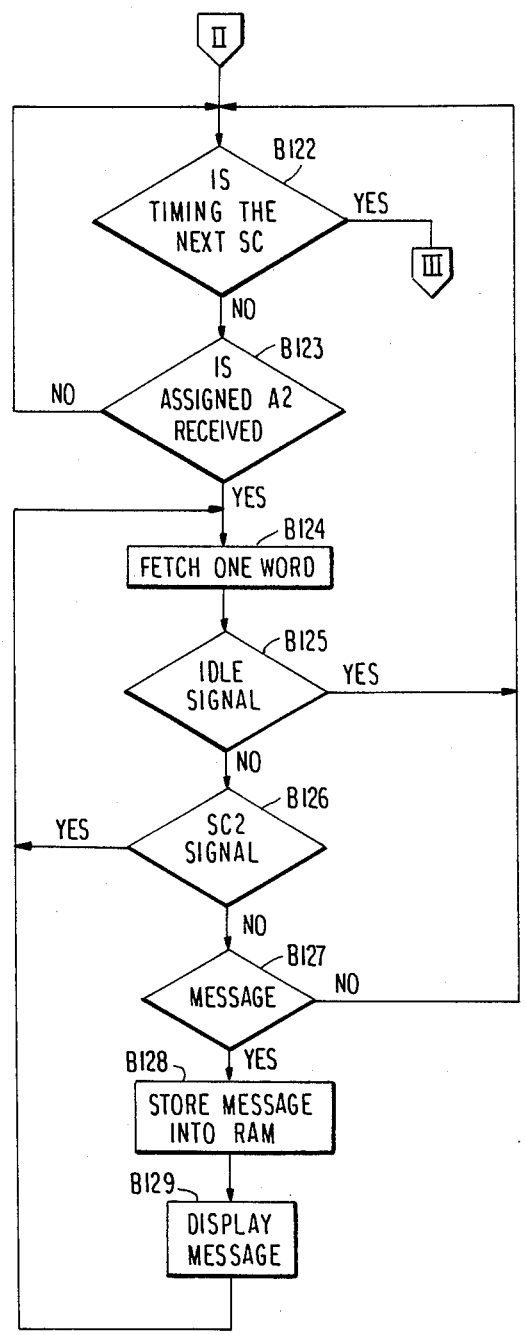

RADIO PAGING SYSTEM CAPABLE OF TRANSMITTING COMMON INFORMATION AND RECEIVER THEREFOR

BACKGROUND OF THE INVENTION

The present invention relates to a radio paging system and, more particularly, to a system for transmitting address signals and messages, as well as information common to a plurality of receivers, and a receiver applicable to such a system.

The art of radio paging systems with display has recently undergone remarkable progress so as to offer a character display service in addition to traditional numerical display services. The character display service allows a considerable quantity of information to be imparted to users of display oriented paging receivers.

The primary problem with such paging receivers is that the display function is wasted except for at the time of the reception of a call. Further, lack of optimal utilization can also be pointed out in regard to the paging station. The paging station does not emit a constant flow of radio waves and thus remains in an idle state except when calls are being originated. (If the pating station is constantly emitting radio waves, it transmit dummy signals except upon the generation of calls)

Additionally, in today's information-intensive society, there is an ever increasing demand for services which offer various kinds of information on a real-time basis and, in this connection, compact terminal equipment is desired.

Furthermore, if two or more address numbers were assigned to each paging receiver with one of these address numbers being common to all receivers so that information might be sent using the common address number, an information service which allows all the receivers to receive common information could be attained. However, the POCSAG code, which is internationally standardized by the CCIR as Radio Paging Code No. 1, hinders the creation of an efficient information service. More specifically, POCSAG code is such that to cut down power consumption at each receiver the indvidual address numbers assigned to the receivers are divided into groups, and are transmitted only at predetermined times, thus only those receivers for which an address number is intended turn on their power sources to receive a call. Common information cannot be imparted to all the receivers unless address numbers and common information each equal in number to the groups are transmitted, resulting in very poor channel utilization. Nevertheless should the address numbers not be grouped, the power consumption at each receiver would be increased.

SUMMARY OF THE INVENTION

It is also therefore an object of the present invention to provide a radio paging system which is capable of offering an information service.

It is another object of the present invention to provide a radio paging system which is capable of offering an information service without lowering the channel utilization efficiency despite the use of POCSAG code.

It is another object of the present invention to provide a paging receiver which is usable for the above objects.

In accordance with the present invention, there is provided a radio paging system comprising: an encoder producing a first code when there follows a string of address codes and message codes, and producing a second code when there follows a string of information codes, the first and second codes being different from each other and positioned at regular time intervals; a transmitter for transmitting a string of codes produced by the encoder; and a paging receiver with a display for receiving the transmitted codes, in synchronism with one of the transmitted first and second codes, which upon the detection of the first code produces an alert signal and displays the message codes only when the address signal which follows the first code is identical to a particular address code and, which, upon detection of the second code, displays the information codes which follow the second code.

BRIEF DESCRIPTION OF THE DRAWINGS

The above and other objects, features and advantages of the present invention will become more apparent from the following detailed description taken with the accompanying drawings in which:

FIGS. 10(a) to 10(d) and 11(a) and 11(b) show respectively a signal format which the receiver of FIG. 7 receives and a procedure for the reception;

FIGS. 14(a) and 14(b) show a signal format which the receiver of FIG. 12 receives and a timing chart associated with the reception, respectively; and FIGS. 15A to 15C are flowcharts representative of operations of the receiver shown in FIG. 12.

DESCRIPTION OF THE PREFERRED EMBODIMENTS

First Embodiment

Figure 1:
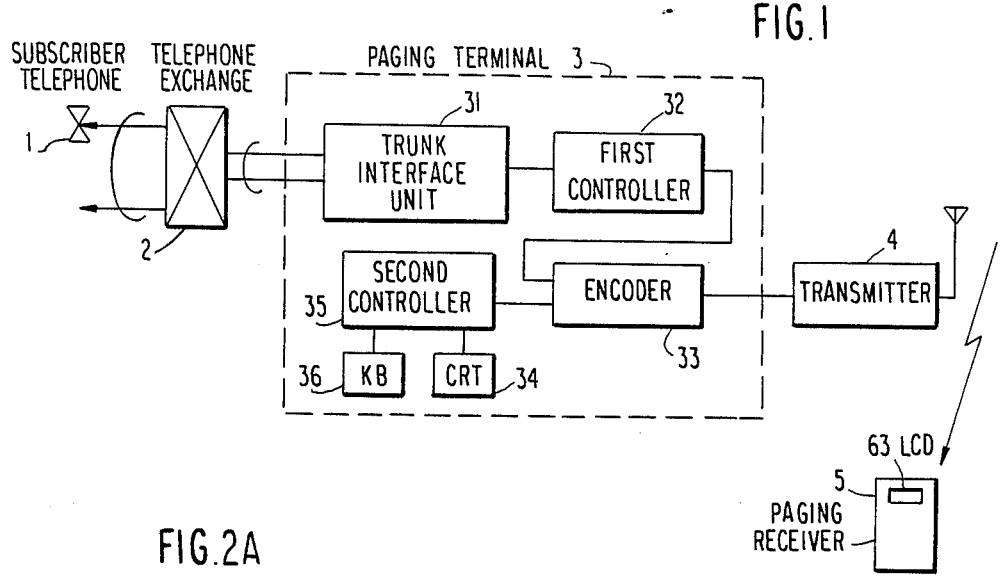
FIG. 1 is a block diagram of a radio paging system in accordance with the present invention.

Referring to FIG. 1 of the drawings, a radio paging system with a display is shown. The system includes a subscriber telephone 1, a telephone exchange 2, a coding device 3, a transmitter 4, and a paging receiver 5.

In the system shown in FIG. 1, ordinary radio paging service is originated via the subscriber telephone 1. Specifically, a person places a call by dialing the telephone number of exchange 2 and an address number which is assigned to the receiver 5. At this instant, the telephone exchange 2 connects itself to the coding device, or paging terminal 3. In the paging terminal 3 a first controller 32 sees if the address number entered via a trunk interface unit 31 is a valid one. If so, the controller 32 sends a validation tone to the exchange 2 informing the caller to enter a message. If the address number is not valid, the controller 32 sends an invalidation tone and rejects any further input.

After confirming the validation tone, the caller manipulates push-buttons on the telephone 1 to enter a message. To conclude the message, a "#" button may be depressed. Under these circumstances, the message is limited to numerals, a small number of signs such as "—", and a blank. The entered address number and message are temporarily stored in the first controller 32, then converted by an encoder 33 to a string of paging signals, which will be described hereinafter, and then forwarded to the transmitter 4. The transmitter 4 modulates a radio carrier wave with the paging signal, the modulated carrier wave being radiated through an antenna. The receiver 5, on the other hand, receives the radiated carrier wave and demodulates it to provide the paging signal. When the receiver 5 senses a signal which agrees with an address number assigned to the receiver 5, it produces an alert tone and displays the message.

The information service of the invention includes data entry means including a keyboard 36 and a cathode ray tube (CRT) 34. The information service uses not only numerals but also alphabetic and other characters. The entered information is temporarily stored in a second controller 35 and, when the paging signal sequence is not being transmitted, applied to the transmitter 4 via the encoder 33 as an information signal sequence. Upon reception of the information signal sequence, the receiver 5 sequentially displays the character data from first to last.

Figure 2A:
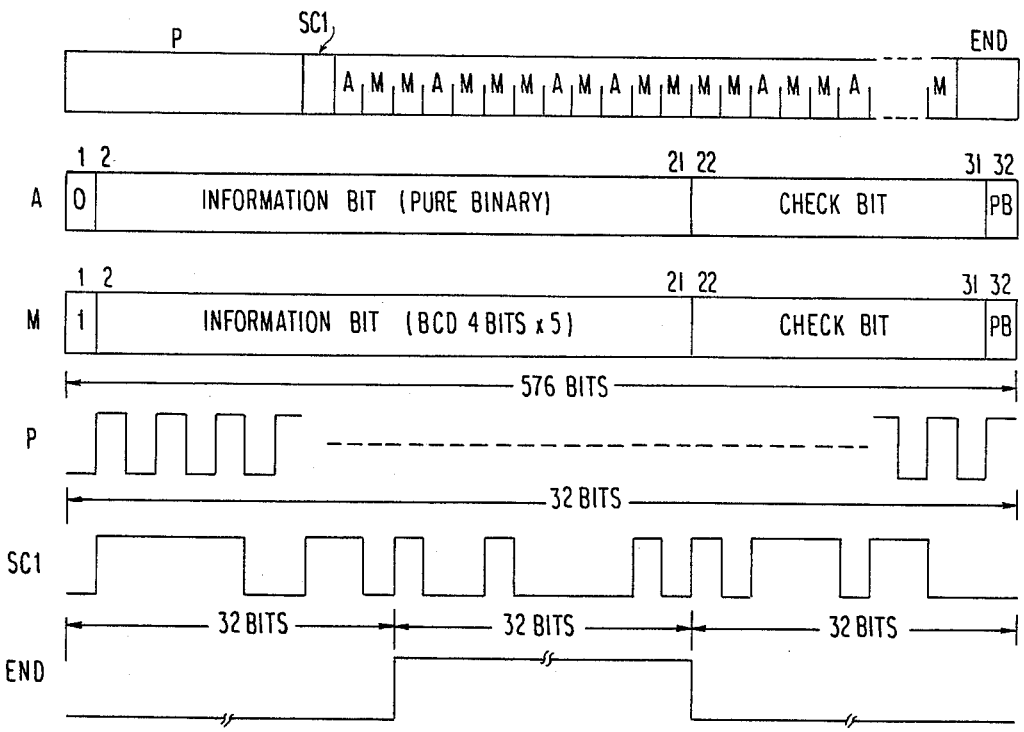
FIGS. 2A and 2B show a first example of a signal format applicable to the system of FIG. 1.

Referring to FIG. 2A, a typical paging signal string which is included in the signal codes applicable to the present invention is shown. As shown, the paging signal sequence comprises a preamble signal P, a first synchronizing signal SC1, address signals A, message signals M, and an end signal END.

A preamble signal P consists of a repetitive ZERO and ONE pattern signal having 576 bits. The preamble signal P is chiefly intended for bit synchronization and is indicative of the start of transmission of a paging signal sequence. The first synchronizing signal SC1 is a 32-bit code which is mainly used for word synchronizing. Each of the address signals A and the message signals M is composed of a 32-bit Bose-Chaudhuri Hocquenghem, (BCH) (31, 21) code and one parity bit which is added to the BCH code; when the most significant bit (MSB) is a ZERO, the signal is an address signal A and, when it is a ONE, the signal is a message signal M. While the information bits of address signal A are purely binary, message signals M are comprised of five digits of four binary-coded decimal (BCD) bits so that one word carries five digits of numerical information. The end signal END consists of 32 consecutive ZERO bits, 32 consecutive ONE bits, and 32 consecutive ZERO bits, and represents the conclusion of a paging signal sequence.

Figure 2B:
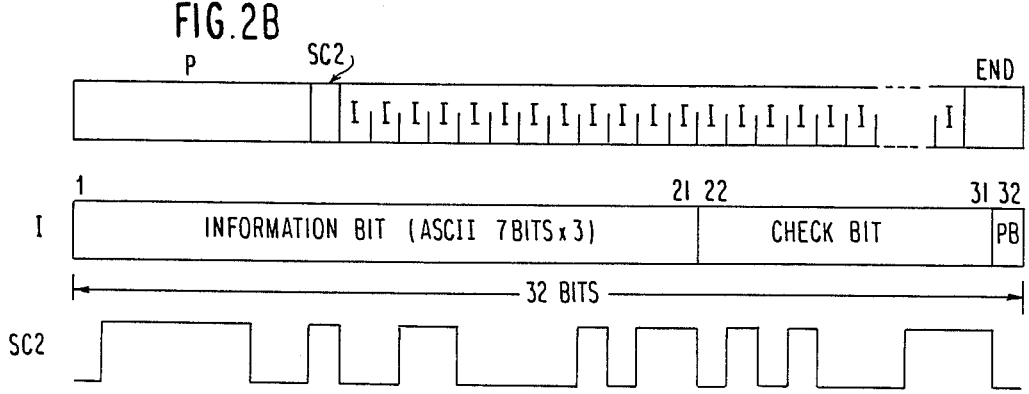

Referring to FIG. 2B, a typical information signal sequence included in the signal codes which the present invention uses is shown. The information signal sequence comprises a preamble signal P, a second synchronizing signal SC2, information signals I, and an end signal END.

The preamble signal P and the end signal E respectively are representative of the beginning and the end of an information signal sequence, as in the paging signal sequence. The second synchronizing signal SC2, like the first one SC1, is a 32-bit code and is adapted for word synchronization. Each information signal I is in a format having a 32-bit BCH (31, 32) code and one parity bit added to the BCH code. The information signal I uses seven Americal National Standard Code for Information Interchange (ASCII) code bits and is capable of transmitting three characters in one word.

The operation of the receiver 5 will now be described in detail.

Figure 3:
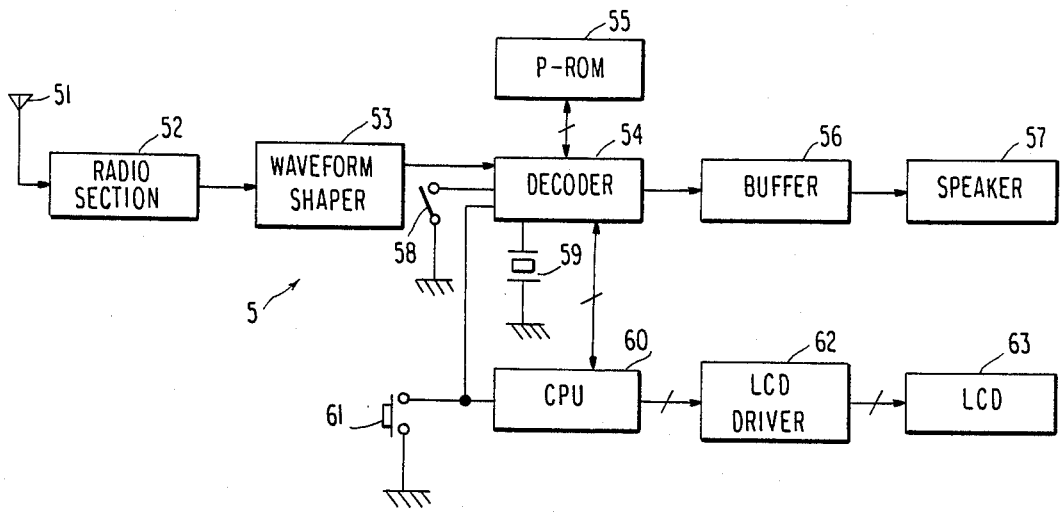
FIG. 3 is a block diagram of a first embodiment of a paging receiver in accordance with the present invention.

Referring to FIG. 3, a specific construction of the receiver 5 is shown. A desired radio carrier wave received through an antenna 51 is amplified and demodulated by a radio section 52, then converted by a waveform shaper 53 into a digital signal, i.e., ONEs and ZEROs, and then applied to a decoder 54. The decoder 54 first receives more than a certain length (e.g. sixteen bits) of the preamble signal P included in the digital signals and, then, enters into reception of the subsequent synchronizing signal SC. Depending upon the kind of synchronizing signal SC, the decoder 54 operates in either a paging signal receive mode or an information signal receive mode.

A programmable read-only memory (P-ROM) 55 stores an address number which is assigned to the receiver 5. In the paging signal receive mode, the decoder 54 compares the received address number with the address number stored in the P-ROM 55 and, if they are identical, delivers a first alarm signal ALM 1 (which will be described) to a central processing unit (CPU) 60 to perform a message receive operation and, at the same time, energizes a speaker 57 via a buffer 56. In response the CPU 60 enters into a message signal receive operation, that is, after the reception of a message signal it delivers data to a liquid crystal display (LCD) driver 62 to display the message on an LCD 63.

In the information signal receive mode, the decoder 54 immediately after the reception of the signal SC2 applies a second alarm signal ALM 2 to the CPU 60. Upon reception of the second alarm signal, the CPU 60 receives an information signal and causes the LCD 63 to display the information via the LCD driver 62. The switch 58 (whose operation will be described below) is a select switch for selecting whether or not to effect the information service, while push-button 61 is usable for resetting the alert tone, reading out a stored message or other purposes.

Figure 4:
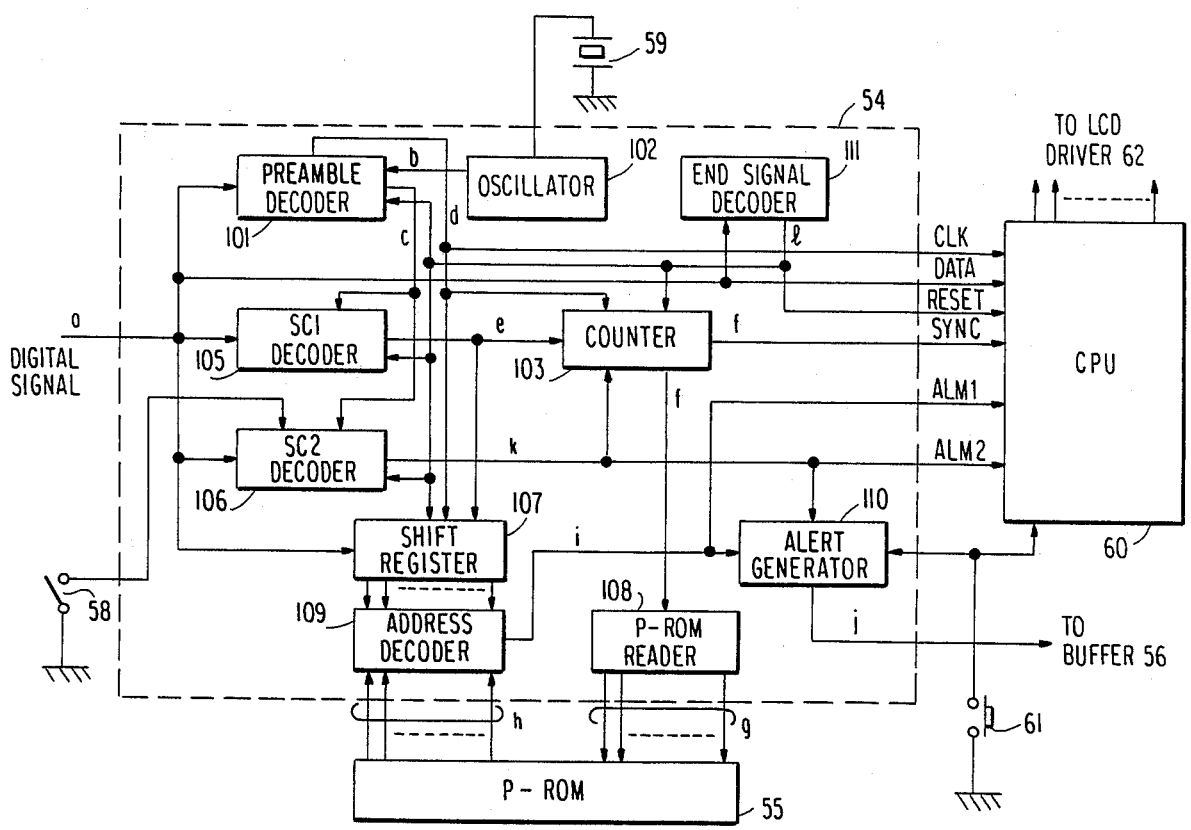
FIG. 4 is a block diagram showing a specific construction of a decoder of the receiver shown in FIG. 3.

Referring to FIG. 4, the operation of the decoder 54 shown in FIG. 3 will be described in detail. The digital signals a coming in from the waveform shaper 53 are applied to a preamble decoder 101 which is adapted to determine whether the signals a include a preamble signal. As previously stated, the preamble signal is a sequence of repetitive ONEs and ZEROs. When the preamble decoder 101 has received sixteen or more bits of a preamble signal in synchronism with a clock b, which is generated by a quartz oscillator 59 and an oscillator 102, it produces a signal c to enable a gate of an SC1 decoder 105 and that of an SC2 decoder 106. In addition, after synchronization has been set up, the preamble decoder 101 applies a CLK signal d to various circuits to provide them with timing. The SC1 decoder 105 serves to detect the SC1 code and the SC2 decoder 106 serves to detect, the SC2 code. Although not shown in the drawing, the SC1 decoder 105 and SC2 decoder 106 are provided with timers so that the gates thereof may be automatically closed when the code SC1 or SC2 has not been detected within a predetermined period of time after the reception of a preamble signal.

As the SC1 decoder 105 detects the SC1 code before the above-mentioned time expires, it delivers an SC1 detection signal e to a counter 103 and a shift register 107. The counter 103, which is a 32-bit counter and is adapted for word synchronization, applies count pulses f to a P-ROM reader 108 (and to the CPU 60) at the same time the P-ROM reader 108 applies read pulses g to the P-ROM 55. Responsive to the read pulses g, the P-ROM 55 delivers an address number code h assigned to the receiver to an address decoder 109. The address decoder 109 compares the address code h with the data stored in the shift register 107 on a thirty-two bit basis and, when they are identical, sends an ALM 1 signal i to an alert generator 110 and the CPU 60. The alert generator 110 responds to the ALM 1 signal i by delivering an alert signal j to a buffer 56, which is adapted to energize the speaker 57. At the same time, the CPU 60 receives DATA signals (the same as the digital signals a) timed to the CLK signal d and count pulses f, thereby receiving a message signal which follows the address signal.

On the other hand, when the SC2 decoder 106 detects the SC2 code within the predetermined period of time, it applies an SC2 detection signal k (ALM 2 signal) to the counter 103 and CPU 60 and, also, to the alert circuit 110. Upon the reception of ALM 2 signal, the alert generator 110 energizes the speaker 57 for a short period of time via the buffer 56 so as to inform the user of the start of reception of information signals. Immediately after the detection of the SC2 code, the CPU 60 receives the DATA signals a as information signals timed to the clock signal d and count pulses f. Count pulses f are produced in response to the SC1 or SC2 code. While storing the DATA signals a in a random access memory (RAM) 207, which will be described, the CPU 60 activates the LCD driver 62 so that the LCD 63 can display the information signals at a speed which is low enough for a person to recognize.

As END signal decoder 111 senses an END signal, it applies a RESET signal 1 to the various circuits within the decoder 54 and to the CPU 60 so as to report the end of a paging signal sequence or that of an information signal sequence. The switch 58 is manipulable to forcibly close the gate of the SC2 decoder 106 to determine whether or not to execute the information service, while the push-button 61 is manipulatable to reset the alert circuit 110 to stop the alert tone. The push-button 61 also fulfills a message reading function as will be described.

Figure 5:
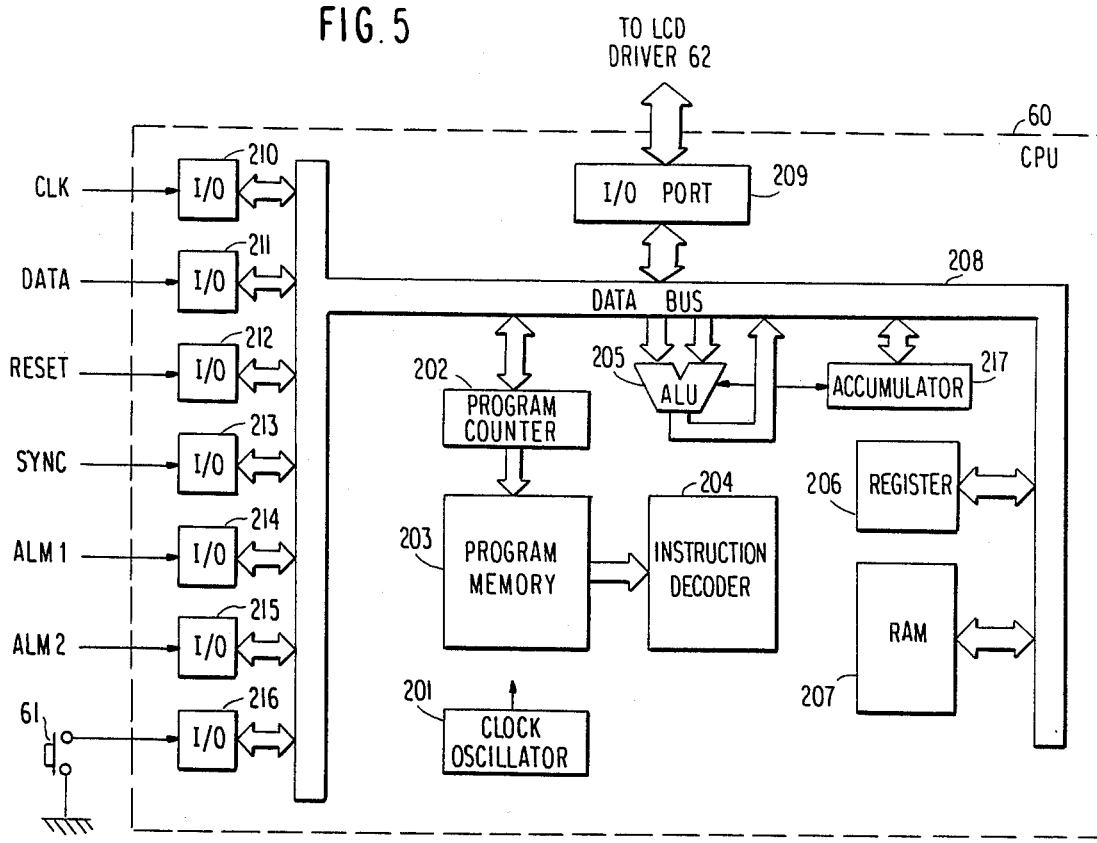
FIG. 5 is a block diagram showing a specific construction of a central processing unit which is included in the receiver of FIG. 3.

Referring to FIG. 5, the operation of the 1-chip CPU 60 will be described in detail. The CPU 60 comprises a system clock oscillator 201 for determining the execution command cycle time, a program counter 202 for designating a content of an address, a program memory 203 for storing a sequence of commands to be executed and allowing the content of an address specified by the program counter 202 to be read out, an instruction decoder 204 for decoding information outputted by the program memory 203 to supply any of the various sections with a control signal which is associated with the command, an arithmetic and logic unit (ALU) 205 for performing arithmetic operations, logic operations and the like, a register set 206 for temporarily storing the content of an address, a stack pointer used for subroutine interruptions, etc., an ordinary RAM 207, a data bus 208, input/output (I/O) ports 209-216, and an accumulator ACC (A-register) 217 used for data exchange between the I/O ports 209-216 and other purposes.

Among the I/O ports 209-216, the port 209 is associated with the LCD driver 62, the port 210 with the CLK signal, the port 211 with the DATA signal, the port 212 with the RESET signal, the port 213 with the SYNC signal, the port 214 with the ALM 1 signal, the port 215 with the ALM 2 signal, and the port 216 with the push-button 61.

Figure 6:
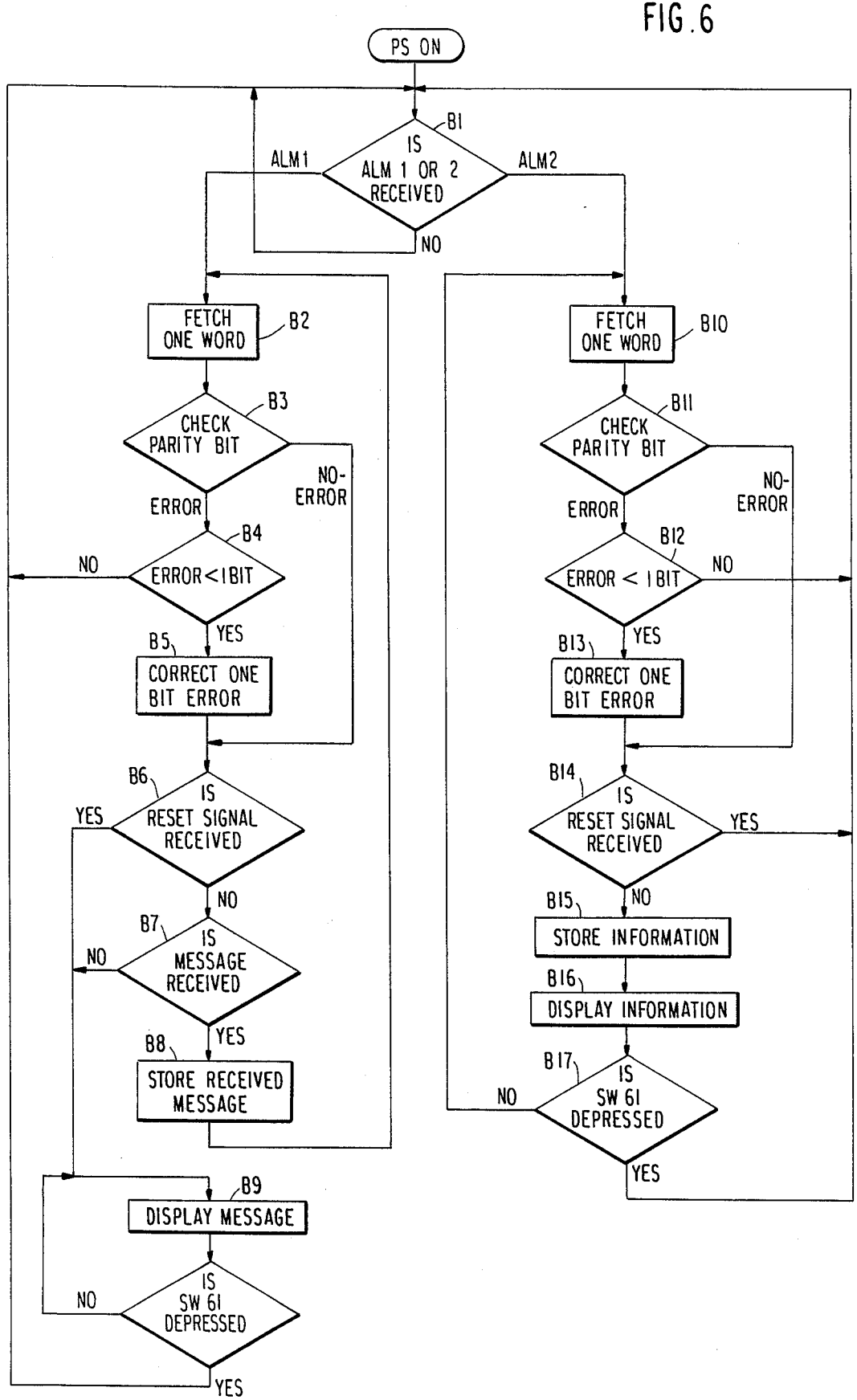
FIG. 6 is a flowchart demonstrating an operation of the receiver of FIG. 3 for receiving the signals which are shown in FIGS. 2A and 2B.

Referring now to FIG. 6, there is shown a flowchart representative of details of the operation of the CPU 60. The CPU 60 awaits entry of data from any of the input ports thereof from the instant when the power supply is turned on. The following description will focus on the procedure which the CPU 60 executes when the decoder 54 has detected its own address number after the synchronizing signal SC1. As the decoder 54 detects the its address number after SC1, it applies the ALM 1 signal to the CPU 60. In response to the ALM 1 signal, the CPU 60 sequentially receives DATA signals timed to the SYNC signal and CLK signal (see STEPS B1 and B2). In the meantime, the CPU 60 performs a word by word check and, if the error is not greater than one bit, corrects the error (STEPS B3-B5). The CPU 60 decides whether the RESET signal is received and, if it is received, immediately displays the message received so far (STEPS B6 and B9). If the reset signal is not received, the CPU 60 determines whether the MSB is a ZERO or a ONE to see if the received data is a message (STEP B7). If the received data is a message, the CPU 60 stores it in the RAM 207 and then receives the next data signal (STEP B8). When the CPU 60 senses an address signal after some messages, it treats the data received up to the immediately preceding data as messages. When the decoder 54 has delivered the ALM 1 signal, the speaker 57 produces an alert tone; when message signals are no longer received, the LCD 63 displays the message (STEP B9). The display of the message may be stopped with the push-button 61 (STEP B9'). The message is stored in the RAM 207 of the CPU 60 and may be read therefrom whenever desired by manipulating the push-button 61.

Next, the operation of the CPU 60 when the decoder 54 detects SC2 will be described. As the decoder 54 detects SC2, it delivers the ALM 2 signal to the CPU 60. In responsie the CPU 60 fetches a DATA signal timed to the SYNC signal and CLK signal (STEP B10) and temporarily stores them in the RAM 207. At this point, as in the case of the SC1 reception, a parity check (STEP B11) and an error correction step (STEPS B12 and B13) are executed. If the CPU 60 receives the RESET signal, it terminates the reception (STEP B14); if it does not, the CPU 60 stores the received information data in the RAM 207 (STEP B15). Again, the received data are applied to the LCD driver 62 in the order of reception and at a speed slow enough for a person to recognize and are displayed on the LCD 63 (STEP B16). The reception procedure ends when the switch 61 is depressed (STEP B17).

In the illustrative embodiment, two different kinds of SC are used, one for the paging service and the other for information service. Alternatively, more than two kinds of SC may be used with one allocated, such as SC2, to stock information, another, such as SC3, to weather information and another, such as SC4, to traffic information, thereby dividing the information service into multiple subservices. In such a multi-subservice scheme, the switch 58 may be designed to select any one of the SCs and, thereby, allow a person to see only the desired information.

SECOND EMBODIMENT

Figure 7:
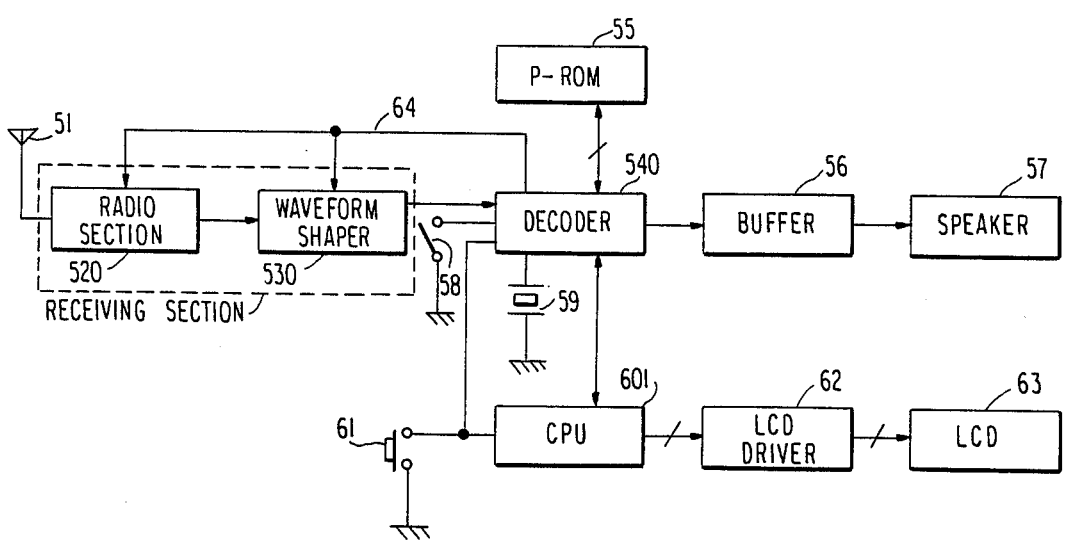
FIG. 7 is a block diagram of a second embodiment of the paging receiver in accordance with the present invention.
Figure 8:
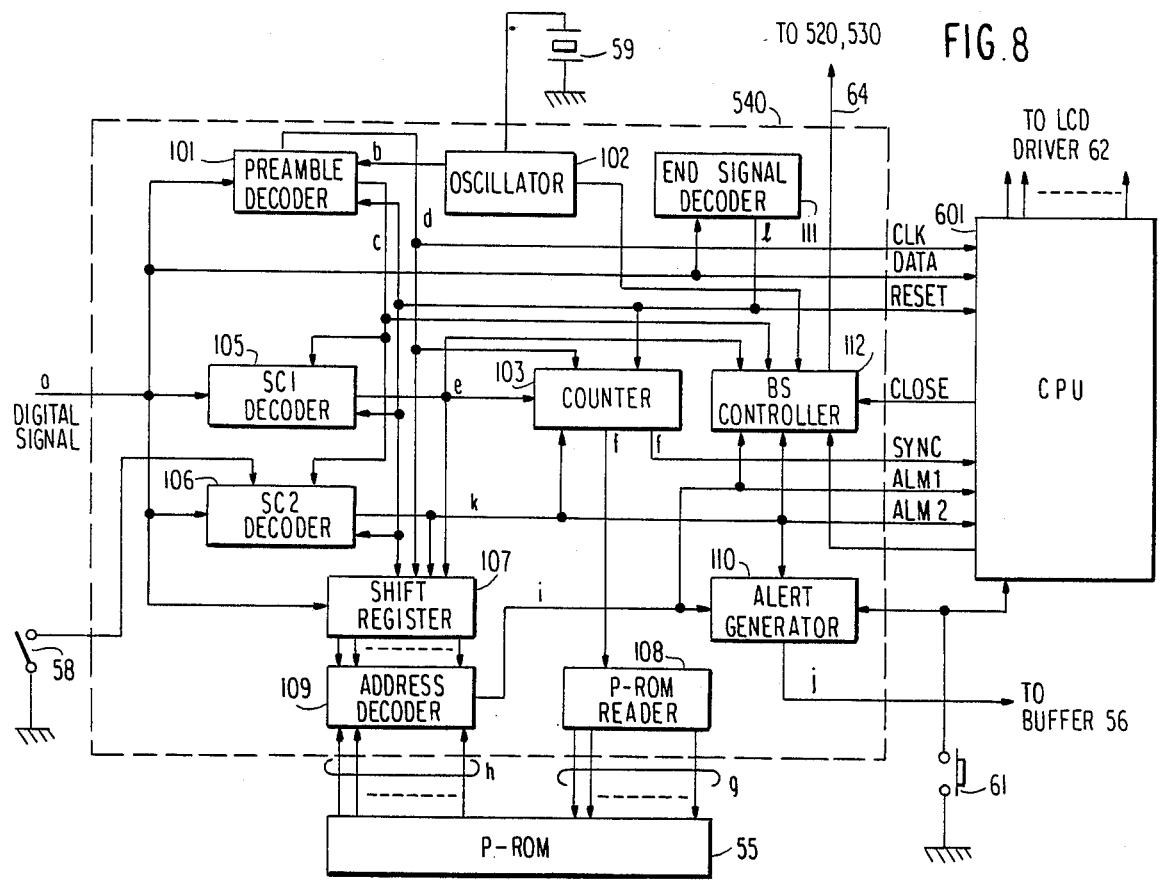
FIG. 8 is a block diagram showing a specific construction of a decoder of the receiver shown in FIG. 7.
Figure 9:
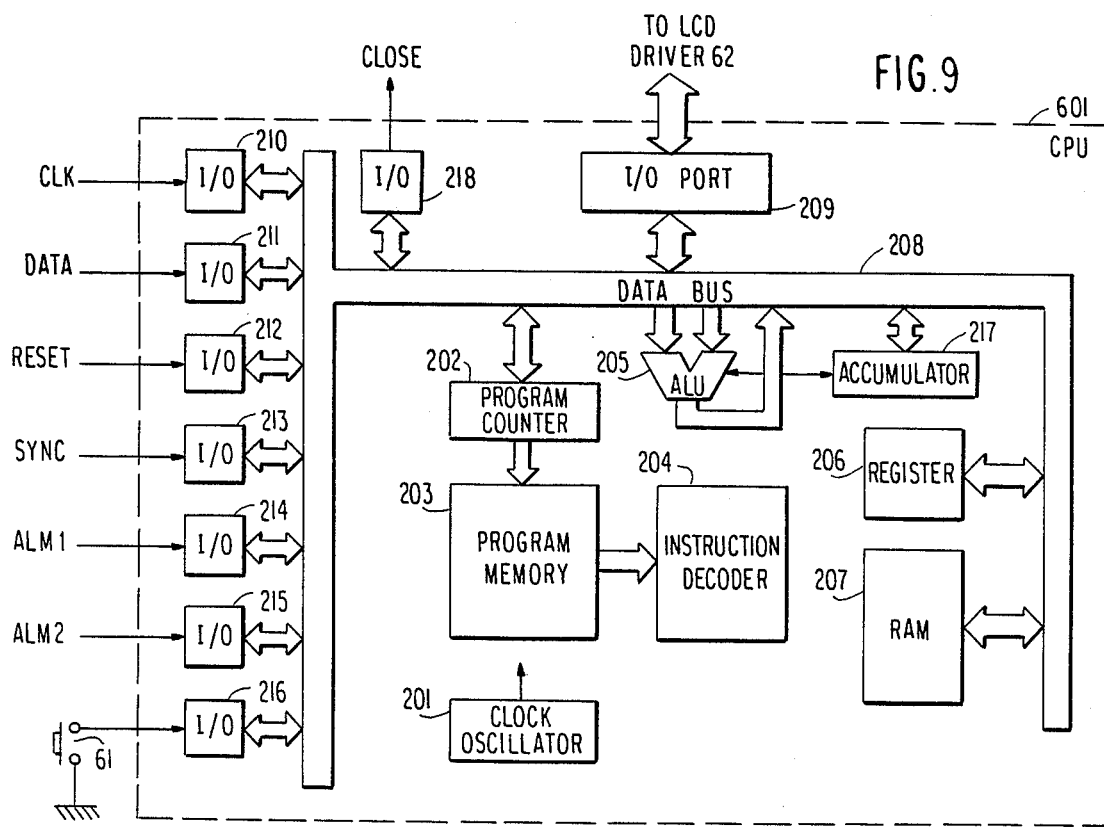
FIG. 9 is a block diagram showing a specific construction of a central processing unit of the receiver shown in FIG. 7.

Referring to FIG. 7, a second embodiment of the receiver of the present invention is shown in a block diagram. The receiver in this particular embodiment differs from the embodiment of FIG. 3 in that an additional control line 64 is installed for controlling the power supply to the radio section 520 and the waveform shaper 530 (which will collectively be referred to as a receiving section here after) for battery saving purposes, and to this end, a battery saving controller 112 is included in a decoder 540. Details of the decoder 540 are shown in FIG. 8 and those of CPU 601 in FIG. 9. Comparing the CPU 601 with the CPU 60 of FIG. 5, it will be seen that the former includes an additional output port 218 for delivering a CLOSE signal which is adapted to report the end of reception to the decoder 540.

FIGS. 10(a) and 10(c) show the signal transmission formats associated with POCSAG code, while FIGS. 10(b) and 10(d) represents the battery saving function which the receiver of FIG. 7 performs during reception. In FIGS. 10(a) 10(c), each format includes a preamble signal P, synchronizing signals SC1, and a sequence of group signals G1–G8 each of which comprises two words and contains either an address signal or a message signal. The address signal belongs to any one of the group signals G1–G8 which correspond in number thereto, and is transmitted only during a time slot assigned to that group. When there is any other address signal to transmit, another synchronizing signal SC1 and another paging signal sequence G1–G8 will be transmitted after the first sequence G1–G8, as illustrated. The address signals and the message signals are formatted in the same manner as those of FIG. 2.

FIG. 10(b) is representative of the battery saving control signal on the control line 64 in the a usual waiting state. This battery saving operation corresponds to the signal format of FIG. 10(a) in which address signals A1 and A1' are not assigned to the receiver in question. First, when a power supply (PS) of the receiver is turned ON, the decoder 540 reads the content of the P-ROM 55 to store a particular group to which its own address number belongs beforehand in the BS controller 112. belongs Before a preamble signal is detected, a control signal from the BS controller 112 is repeatedly turned ON and OFF so that during radio section power supply ON times $t_1$ and OFF times T, a preamble signal can be received during any ON period of the BS controller 112. Upon detection of a preamble signal, the ON period is prolonged by at least one frame (interval between SCs) responsive to a signal c and then synchronizing signal reception begins.

As the SC1 decoder 105 senses SC1, the receiving section is continuously turned off by a signal e until the transmission time assigned to a predetermined group (e.g. G5) is reached. As soon as that particular transmission time is reached, the receiving section is turned on to begin receiving its own address signal. If its own address signal is not sensed, then the receiving section is turned off and turned on again at the transmission timing of the next synchronizing signal SC1. At that time, if a synchronizing signal SC1 is received, the above procedure will be repeated.

FIG. 10(d) is representative of an operation for supplying power to the receiving section when an address signal is received. The battery saving operation of FIG. 10(d) corresponds to the signal format of FIG. 10(c) in which an address signal A1 is assigned to the receiver in question. When the address decoder 109 has received an address signal during the transmission timing assigned to the group (G5), the ON period of the receiving section is prolonged by a signal i to allow the CPU 601 to receive a message signal. Specifically, the CPU 601 identifies a message based on the MSB and continuously receives it so long as it is continuously transmitted. When the message signal terminates, the CPU 601 delivers a CLOSE signal to turn off the receiving section again.

Referring to FIG. 11, there is shown the operation of the receiver associated with the information service. As a synchronization signal SC2 is received after a preamble signal, the receiver section is maintained in its ON state by a signal k with no regard to the group of the address signals until a CLOSE signal from the CPU 601 arrives or until the SC2 decoder 106 ceases to periodically sense the synchronizing signal SC2. In the meantime, the CPU 601 continuously receives an information signal and displays it on the LCD 63. The flowchart shown in FIG. 6 also applies to the CPU 601 except that the CPU 601 delivers a CLOSE signal to the decoder 540 at the end of message signal reception or the end of information signal reception, and in that the data associated with synchronizing signals SC1 or SC2 is not displayed when the latter is received. It should be noted that concerning POCSAG code, an IDLE signal (32-bits long "01111010100010011100000110010111") is substituted for the END signal which was described in relation to the first embodiment.

Third Embodiment

Figure 12:
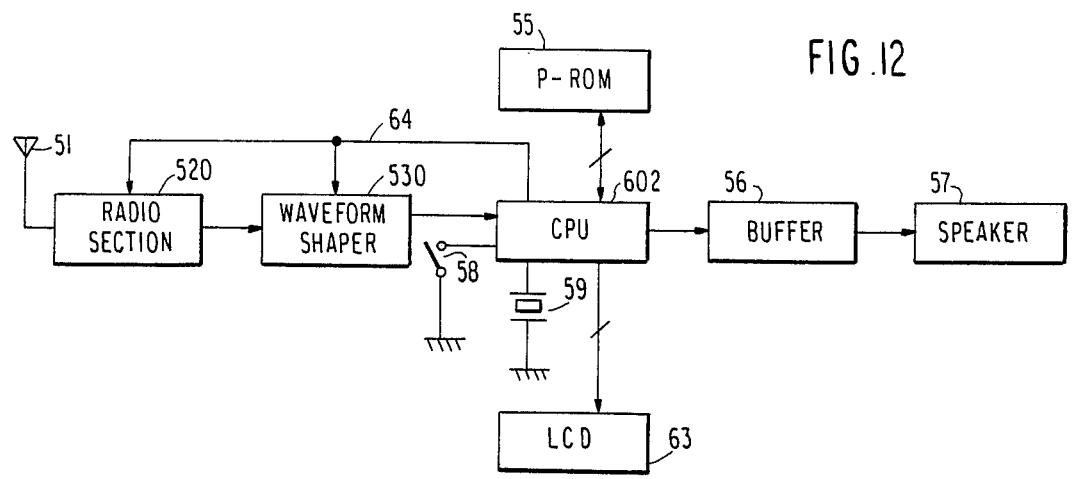
FIG. 12 is a block diagram of a third embodiment of the paging receiver in accordance with the present invention.

The third embodiment is a further extended version of the first and second embodiments. In this particular embodiment, the functions which are fulfilled by the decoder and LCD driver in the first and second embodiments are assigned to a CPU 602 (see FIG. 12). The P-ROM 55 stores two different address numbers, i.e. a first address number (A1) for paging and a second address number (A2) for information data reception.

Figure 13:
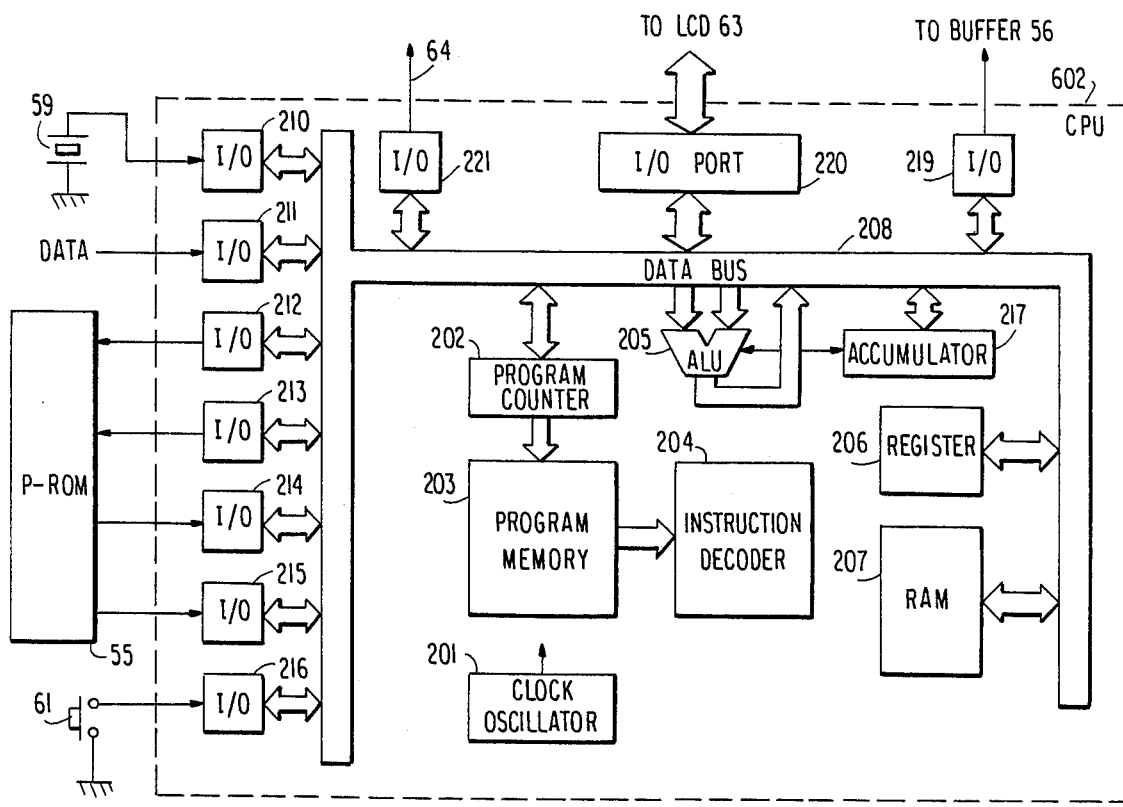
FIG. 13 is a block diagram of a specific construction of a CPU which is included in the receiver of FIG. 12.

Referring to FIG. 13, a specific construction of the CPU 602 is shown, which in respects to I/O ports differs from those of the first and second embodiments. Specifically, the quartz oscillator 59 for synchronization and counting signals is directly connected to a port 210. Ports 212, 213, 214 and 215 are connected to the P-ROM 55. Ports 212 and 213 are respectively for outputting address number read request signals associated with paging and information data; while ports 214 and 215 are respectively for inputting data associated with the address number for paging, and the address number for information. Additionally the output port 220 has an LCD driver function and is directly connected to the LCD 63.

A port 221 is available for outputting a battery saving signal which directly turns on and off the receiving section (520, 530), and a port 219 is available for outputting an alert signal to buffer 56. While the signal format employed is the POCSAG code, as in the second embodiment, during transmission of information service data which follows the SC2, an address signal (A2) and then a message signal (M) is transmitted. The information unit is implemented with the ASCII 7-bits length. Specifically, the MSB is used to discriminate between an address signal and a message signal. There are twenty information bits in the message code M (FIG. 2A), and thus the amount of information which one message word can carry is 5 four-bit BCD codes. There are 21 information bits in the message signal of the information signal string (FIG. 2B), and thus the amount of information which can be carried by one word is 3 seven-bit ASCII type characters.

Figure 15B:
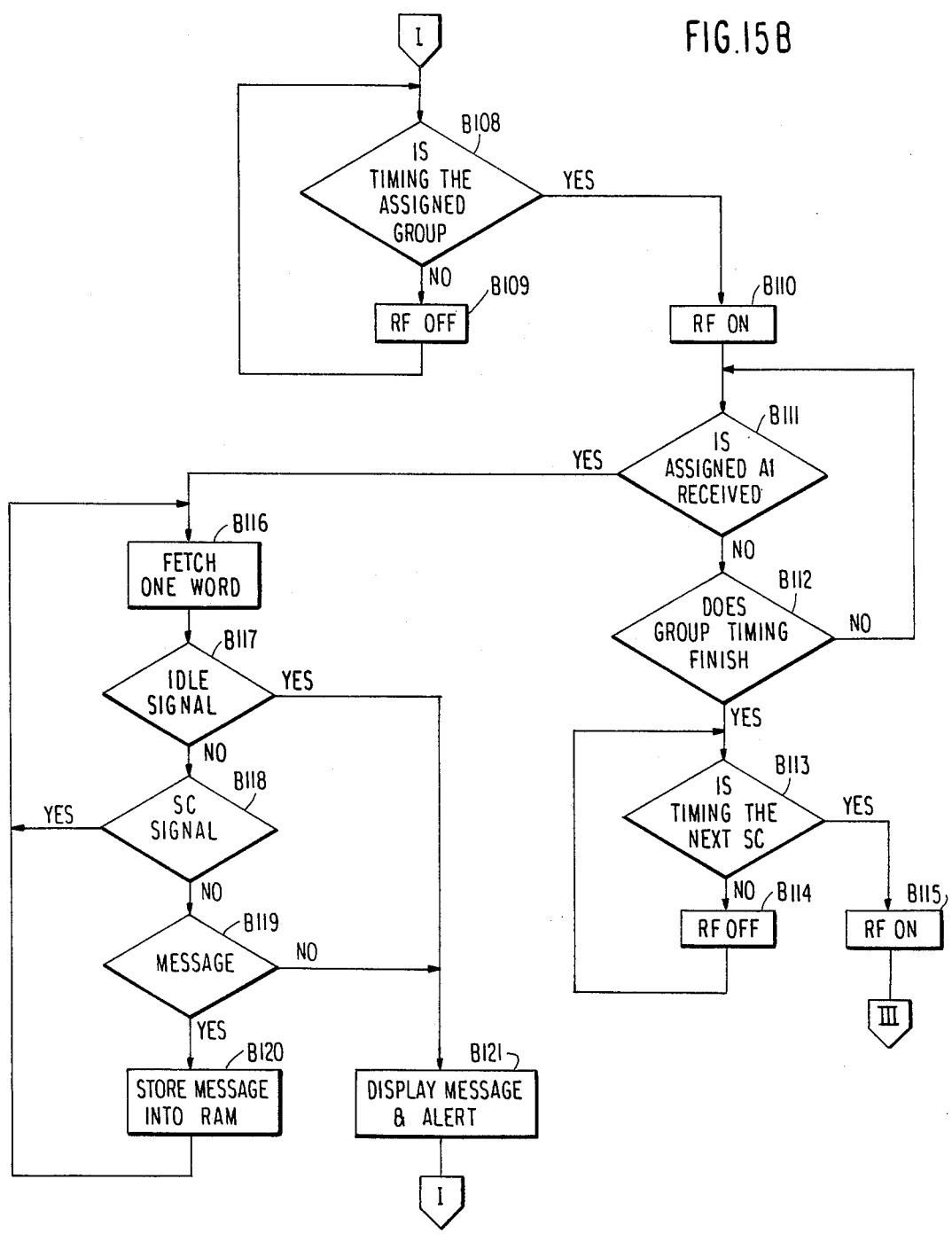

Now, an actual reception operation will be described referring to the timing chart of FIG. 14 and the flowcharts of FIGS. 15A-15C, the latter being associated with the CPU 602. After the power supply (PS) has been turned on, the receiver supplies power to the receiving section intermittently at the period of OFF for a time T and that of ON for a time $t_1$ (STEPS B101, B102, B103 and B105), to sense whether a preamble signal is detected during each ON state (STEP B104). When a preamble signal has been detected, the receiver checks for SC over a time $t_2$ (STEPS B106 and B107); if SC1 is detected, the receiver enters into group-by-group reception (I) and, if SC2 is detected, into a simultaneous reception (II).

In the situation shown in FIG. 14, since SC1 follows the preamble signal, the receiver starts on group-by-group reception (jumping to STEPS B108 and onward). First, the receiving section is turned off until the transmission time which is assigned to its own address number (here G5) is reached (STEPS B108 and B109) and, in the meantime, reception of a signal identical with the first address signal (A1) is checked for (STEPS B111 and B112). If no such signal is received, the receiving section is turned off again until the next SC transmission timing (STEPS B113, B114 and B115) and, then, the operation returns to the SC receiving step (STEP B106).

After the first address signal A1 has been received, a message signal(s) is received and stored in the RAM until an idle signal is received or until assigned other than a message signal is received (STEPS B117, B119 and B120). After the completion of the message signal, the speaker is energized and the message is displayed on the LCD (STEP). In this instance, if SC appears in the received signal, then the SC data is prevented from being stored in the RAM (B118). In the situation shown in FIG. 14, since A1' is transmitted at the timing of G5 after SC1, the speaker is not energized and the receiving section is kept turned off until the next SC transmission timing.

Since SC2 is transmitted at the next SC transmission timing, the receiver enters into a simultaneous reception flow B122 (FIG. 15C). In this case, until the next SC transmission timing after the reception of SC2, reception of the second address A2 signal is checked for throughout all the groups (STEPS B122 and B123). If this signal is received, a message is stored in the RAM and repeatedly displayed on the LCD until another address signal is received. However, when SC2 is received, its data is not displayed (STEPS B124, B125, B126, B127, B128 and B129).

If desired, an arrangement may be made such that the speaker and the display are activated at the time of simultaneous reception as at the time of group-by-group reception. As seen from FIGS. 10(a), 10(c), 11(a), or 14(a), a synchronizing signal is transmitted periodically after the preamble signal. The kind of the synchronizing signal may be varied such that sometimes group-by-group reception occurs and sometimes simultaneous reception occurs. This expands the application of the present invention from a single paging service, to both a single paging service and a group paging service.

In summary, it will be seen that the present invention allows an existing paging receiver with a display to fulfill not only a simple paging service but also a wide variety of information services by using a plurality of synchronizing codes and assigning one of them to a paging service and another to an information service. The synchronizing codes in accordance with the present invention are provided with a word synchronizing function to eliminate the need for extra synchronizing signals and, thereby, enhance efficient use of the channel. In addition, at the receiver, battery saving is effected and, further, reception is not performed even after the detection of a synchronizing signal except at its time of transmission of the own group, all the groups can be received, thus enhancing the efficient use of the channel in the event of a group paging service.

What is claimed is:

1. A radio paging system comprising:
    paging terminal means including an encoder for producing, as an output thereof, one of a first code, followed by a string of address codes and message codes, and a second code followed by a string of information codes, said first and second codes being different from each other and positioned at regular time intervals;
    a transmitter for transmitting a signal including the output of said encoder; and
    a paging receiver for receiving said transmitted signal, and for establishing signal reception synchronization in response to a portion of said transmitted signal including said one of said first and second codes, said receiver comprising;
    means for detecting said first code;
    means for comparing said address codes with an address code assigned to said receiver;
    means for producing an alarm signal and for displaying said message codes in response to the detection of said first code and the detection of coincidence between said address code and said address code assigned to said receiver;
    means for detecting said second code; and
    means responsive to detection of said second code for effecting the display of said information codes.

2. A radio paging system as claimed in claim 1, wherein said first and second codes are synchronizing codes, and further including means for using said first and second codes for word synchronization.

3. A radio paging system as claimed in claim 1, wherein said paging receiver further comprises:
    an antenna for receiving radio carrier waves;
    a radio section for amplifying and demodulating said radio carrier waves;
    a waveform shaper for converting said amplified, demodulated radio carrier waves into a digital signal.

4. A radio paging system as claimed in claim 3, wherein said paging receiver further comprises:
    a programmable read-only memory for storing said address code assigned to said receiver;
    a decoder for receiving said digital signal, detecting one of said first code and said second code and operating in a paging signal receive mode in response to said first code and in an information receive mode in response to said second code, said decoder including means for comparing said address code received from said transmitter with said address code stored in said programmable read-only memory and assigned to said receiver, and means for producing a first alarm signal in response to detection of said first code or a second alarm signal in response to detection of said second code, said first alarm signal being produced upon agreement of said received address code with said stored address code;

a central processing unit for receiving said alarm signals; and, in response to said first alarm signal, performing a message signal receive operation and delivering resulting message signal data to a display means; and in response to said second alarm signal, performing an information signal receive operation and displaying said information code on said display means.

5. A radio paging system as claimed in claim 4 wherein said paging receiver further comprises:
switch means coupled to said decoder for selecting whether or not to display said information code.

6. A radio paging system as claimed in claim 5, wherein said decoder further comprises:
a preamble decoder for determining whether said digital signal includes a preamble signal and for producing a gate enable signal and a clock signal upon reception of said preamble signal;
a first synchronizing signal decoder for detecting a first synchronizing signal as said first code upon receiving said gate enable signal from said preamble decoder, and for producing a detection signal;
a counter adapted for word synchronization for applying counter pulses to a programmable read-only memory reader and said central processing unit, said counter receiving said detection signal from said first synchronizing signal decoder;
a shift register receiving said digital signal, said clock signal from said preamble decoder, and said first synchronizing signal, for storing said address code;
an address decoder for comparing said address code stored in said shift register with said address code assigned to said receiver which is received from said programmable read-only memory, and for producing said first alarm signal upon coincidence;
an alert generator for producing an alert signal in response to said first or second alarm signal;
a second synchronizing signal decoder for detecting said second synchronizing signal as said second code upon receiving said gate enable signal from said preamble decoder and transmitting said second alarm signal to said counter, said central processing unit and said alert generator;
an end signal detector for sensing an end signal and, in response, transmitting a reset signal to said central processing unit, said preamble decoder, said first synchronizing signal decoder, said second synchronizing signal decoder and said shift register.

7. A radio paging system as claimed in claim 6, wherein said decoder further comprises:
a battery saving controller means for controlling the supply of power to said radio section and said waveform shaper according to a predetermined timing pattern including "on" and "off" periods, said battery saving controller means operating in response to said gate enable signal to extend said "on" period to permit detection of said first or second synchronizing signals.

8. A radio paging system as claimed in claim 7, wherein said battery saving controller means operates in response to said first synchronizing signal to initiate an "off" period until reaching a transmission time assigned to a preselected address code.

9. A radio paging system as claimed in claim 8, wherein said central processing unit further comprises:
an output port for delivering a close signal to report the end of signal reception to said battery saving controller means.

10. A radio paging system as claimed in claim 6, wherein said central processing unit further comprises:
input/output ports associated with a display driver, said clock signal, said digital signal, said reset signal, said count pulses from said counter, said first alarm code, and said second alarm code.

11. A radio paging system comprising:
paging terminal means including an encoder for producing one of a first synchronizing signal, followed by a string of address signals and message signals, and a second synchronizing signal followed by a string of information signals;
a transmitter means for transmitting said signals produced by said encoder; and
a receiver means, comprising;
means for detecting said first synchronizing signal;
means responsive to said detecting means for supplying power to at least a radio section of said receiver only at a predetermined transmission timing;
means for detecting said address signal;
means for detecting said second synchronizing signal;
means responsive to said address signal detecting means for displaying a following message signal; and responsive to said second synchronizing signal detecting means for displaying a following information signal;
said means responsive to said first synchronizing signal detecting means being further responsive to said means for detecting said second synchronizing signal for continuously supplying power to at least said radio section upon detection of said second synchronizing signal, and in the absence of either said first synchronizing signal or said second synchronizing signal, intermittently supplying power to at least said radio section until one of said first synchronizing signal and said second synchronizing signal is detected.

* * * * *

UNITED STATES PATENT AND TRADEMARK OFFICE
CERTIFICATE OF CORRECTION

PATENT NO. : 4,783,654
DATED : November 8, 1988
INVENTOR(S) : ICHIKAWA

It is certified that error appears in the above-identified patent and that said Letters Patent is hereby corrected as shown below:

Column 1, line 24, delete "pating" and insert --paging--.
Column 1, lines 41 and 42, delete "is such that" and insert --so constituted that--.
Column 7, line 46, delete "A1 and A1'" and insert --A1' and A1"--.

Signed and Sealed this

Eighth Day of August, 1989

Attest:

DONALD J. QUIGG

Attesting Officer

Commissioner of Patents and Trademarks